United States Patent [19]

Kwun et al.

[11] Patent Number: 4,497,209

[45] Date of Patent: Feb. 5, 1985

[54] NONDESTRUCTIVE TESTING OF STRESS IN A FERROMAGNETIC STRUCTURAL MATERIAL UTILIZING MAGNETICALLY INDUCED VELOCITY CHANGE MEASUREMENTS

[75] Inventors: Hegeon Kwun; Cecil M. Teller, II, both of San Antonio, Tex.

[73] Assignee: Southwest Research Institute, San Antonio, Tex.

[21] Appl. No.: 513,059

[22] Filed: Jul. 12, 1983

[51] Int. Cl.³ ............................................... G01N 22/00
[52] U.S. Cl. ........................................ 73/601; 324/209
[58] Field of Search ............... 73/601, 570, 760; 324/209

[56] References Cited

U.S. PATENT DOCUMENTS

| 2,998,536 | 8/1961 | Dubsky et al. ............... 310/15 |
| 3,577,774 | 5/1971 | Steffens . | |
| 3,872,378 | 3/1975 | Shiraiwa et al. ............... 324/37 |
| 4,080,836 | 3/1978 | Thompson et al. ............... 73/597 |
| 4,167,878 | 9/1979 | Bottcher et al. ............... 73/601 |
| 4,309,905 | 1/1982 | Maizenberg et al. ............... 73/601 |
| 4,314,202 | 2/1982 | Okubo ............... 324/207 |

FOREIGN PATENT DOCUMENTS 2053185  4/1971  France ............................ 73/601

*Primary Examiner*—Jerry W. Myracle
*Attorney, Agent, or Firm*—Gunn, Lee & Jackson

[57] ABSTRACT

This disclosure relates to a nondestructive method of measuring stress in a ferromagnetic structural material. One method involves the measurement of the change in ultrasonic velocity induced by an externally applied magnetic field; the method enables nondestructively determining the magnitude, the direction, and the sign (i.e., tensile or compressive) of a stress in a ferromagnetic material. The magnetically induced velocity change of an ultrasonic wave is caused by the magnetoelastic coupling in the ferromagnetic material. This magnetically induced velocity change is characteristically dependent on the magnitude and the sign of the stress and also on the relative orientation of the stress, the magnetic field, and the polarization and propagation direction of the ultrasonic wave. The dependence of magnetically induced velocity changes can be utilized for nondestructive stress measurements. In one version, for measuring bulk stresses, either a longitudinal ultrasonic wave or a shear ultrasonic wave is used. In another version, for measuring surface stresses, a surface ultrasonic wave is preferably used. By using surface waves at several different frequencies, a stress gradient can also be determined.

16 Claims, 6 Drawing Figures

NONDESTRUCTIVE TESTING OF STRESS IN A FERROMAGNETIC STRUCTURAL MATERIAL UTILIZING MAGNETICALLY INDUCED VELOCITY CHANGE MEASUREMENTS

BACKGROUND OF THE DISCLOSURE

The trend in modern structural design has been to utilize higher strength materials to meet higher design stress goals while reducing overall material costs. However, these trends have been accompanied by an inherent risk of structural failure resulting from an inherent loss of ductility and, in many cases, a reduction in design safety factors. Residual stresses inadvertently introduced during manufacturing and fabrication processes such as forming and welding can no longer be ignored; such initial stresses must be carefully determined and considered to establish safe loadcarrying capability of modern structures. This is because residual and applied stresses may combine to exceed design allowables. Therefore, in recent times there is greater interest in the methods for measuring both applied and residual stresses, especially nondestructive methods of residual stress measurement.

In metals, a widely accepted nondestructive residual stress measurement method is x-ray diffraction, but it has several practical limitations and can only measure stress within a few thousandths of an inch of the surface. More recently, because of the ability of acoustic energy to penetrate much deeper into most metallic materials, there has been considerable development activity associated with the ultrasonic method for measuring bulk residual stresses, especially the shear wave birefringence technique. This ultrasonic method, based on the acoustoelastic effect, has shown good potential for use in measuring bulk residual stresses in homogeneous and isotropic materials. However, practical application of ultrasonics has been severely limited by material variables such as preferred grain orientation, composition, prior magnetic history (for example in steels) and inhomogeneity which, in some cases, can totally mask the acoustoelastic effect.

This invention relates to a new ultrasonic method for measuring stresses in ferromagnetic materials using the magnetoelastic effect. One version of this method utilizes the stress dependence of the change in ultrasonic velocity induced by an externally applied magnetic field. As a result of the investigations underlying the present invention, it is believed that the velocity changes of ultrasonic shear waves induced by externally applied magnetic fields are characteristically dependent on the relative orientation of the stress, the shear wave polarization, and the magnetic field, as well as on the magnitude and sign of the stress, i.e., tensile or compressive. Importantly, it appears that the magnetically induced velocity change (MIVC) is insensitive to the elastic anisotropy caused by preferred grain orientation. Further, ensuing investigations suggest that MIVC of ultrasonic longitudinal and surface waves is also characteristically dependent on the relative orientations of the stress, the polarization and the propagation direction of the ultrasonic wave, and the magnetic field, as well as on the magnitude and sign of the stress.

An example of the characteristic stress dependence of MIVC is shown in FIGS. 1 and 2 which were obtained with 4.5 MHz ultrasonic shear waves in A-36 steel specimens under uniaxial tensile stresses. FIG. 1A is for the case where the shear wave polarization ($\vec{S}$), the magnetic field ($\vec{H}$) and the stress ($\vec{T}$) are all parallel (abbreviated $\vec{S} \parallel \vec{H} \parallel \vec{T}$). Similarly, FIG. 1B is for the case where $\vec{S}$ and $\vec{H}$ are parallel but the two are perpendicular to $\vec{T}$ (abbreviated $\vec{S} \parallel \vec{H} \perp \vec{T}$). In the graphs, the magnetically induced velocity change is $\Delta V$. $\Delta V$ is defined as $\Delta V = V_H - V_H$ where $V_H$ is the velocity at field H and $V_O$ is the velocity at H=O. Both graphs are normalized for $V_O$ as observed on the abscissa. The MIVC curves in FIG. 1A and 1B are identical at T=O. However, as the tensile stress increases, the curves in FIG. 1B exhibit distinctly different behavior from those in FIG. 1A. The decrease in the magnetically induced velocity changes with stress is much larger for $\vec{S} \parallel \vec{H} \perp \vec{T}$ than for $\vec{S} \parallel \vec{H} \parallel \vec{T}$, and the curve at T=20 KSI shows a characteristic minimum for $\vec{S} \parallel \vec{H} \perp \vec{T}$. The characteristic dependence of MIVC on the stress magnitude such as shown in FIG. 1B is the basis for determining the magnitude of an unknown tensile stress.

The MIVC curves in FIGS. 1A and 1B are redrawn in FIGS. 2A and 2B to show their dependence on the relative orientations of $\vec{S}$, $\vec{H}$ and $\vec{T}$. FIGS. 2A and 2B show the MIVC curves for fixed stresses of 10 KSI and 20 KSI, respectively. As shown in FIGS. 2A and 2B, the velocity change induced for a given H value is largest for $\vec{S} \parallel \vec{H} \parallel \vec{T}$ and smallest for $\vec{S} \parallel \vec{H} \perp \vec{T}$. When T is at an angle to $S \parallel H$ between 0° to 90°, the corresponding velocity change value lies between the two extreme values obtained for $\vec{S} \parallel \vec{H} \parallel \vec{T}$ and $\vec{S} \parallel \vec{H} \perp \vec{T}$, respectively. Such characteristic relative orientation dependence of MIVC makes the determination of the direction of a stress possible. Changes in MIVC of ultrasonic shear waves as a function of both uniaxial tensile and compressive stresses and relative orientations of T, S and H in A-36 steel can be found in detail in references H. Kwun, "Stress Measurement in Ferromagnetic Material", Final Report, SwRI Project 15-9297, August (1982); H. Kwun and C. M. Teller, "Tensile Stress Dependence of Magnetically Induced Ultrasonic Shear Wave Velocity Change in Polycrystalline A-36 Steel", Appl. Phys. Lett. 41, 144 (1982).

In addition to the stress, the characteristics of MIVC are in general a function of the magnitude and the sign, i.e., positive or negative, of the magnetostriction coefficient of a material and the frequency and the wave mode, i.e., longitudinal, shear or surface, of an ultrasonic wave employed. Therefore, to determine an unknown stress in a given structural member by the present invention, calibration MIVC curves should be obtained first over a range of applied stresses using the same nominal alloy material; the alloy need not be identical, particularly in terms of preferred orientation or elastic anisotropy on calibrating for the same ultrasonic wave mode and frequency as that to be used in a test. Basically, an unknown stress in a structural member is determined by comparing measured MIVC curve(s) in the structural member under testing with a set of calibration MIVC curves obtained in the specimen material.

To determine bulk, surface as well as gradient of stresses, MIVC curves of an ultrasonic shear or longitudinal wave as well as those of ultrasonic surface waves at several different frequencies are required. Usually the penetration depth of a surface wave is approximately equal to the wavelength of the wave; stresses at different depths below the surface of a material can be sensed using surface waves of different frequencies.

The method proposed in this invention utilizes a C-shaped magnet having a pair of pole faces which are positioned adjacent to a structural member under testing. This magnet forms magnetic field lines in the test specimen tangential to the surface of the specimen. Appropriate ultrasonic transducer(s) are attached to the specimen. For the case of ultrasonic surface wave, two transducers are required; one is used as the transmitter and the other as the receiver of the surface wave. Ultrasonic transducers are coupled to the member using an appropriate couplant, such as oil, water or a shear wave couplant having a high viscosity. The applied magnetic field is measured using a tangential Hall effect probe placed adjacent to the ultrasonic transducer, and the change in velocity (more specifically the change in the time-of-flight) of the ultrasonic wave as a function of magnetic field can then be obtained. For accurately measuring the change in velocity, either a pulse-echo overlapping technique or a relative phase (to a reference rf wave) measuring technique can be used. One such technique is described in R. J. Blume, "Instrument for Continuous High Resolution Measurement of Changes in the Velocity of Ultrasound", Rev. Sci. Instrum. 34, 1400 (1963). In the case of surface waves, the use of a relative phase measuring technique is the only choice since there is only one received signal and there are no echoes to overlap.

It has been found that magnetic hysteresis effect on the magnetically induced velocity changes is negligible in most cases. It appears also that there is no difference by reversing the magnetic field.

The procedure set forth hereinbelow particularly finds ready application in testing structural components in an assembled framework and the like. Consider the situation where a support framework is fabricated for heavy equipment. It is possible to use the procedure described herein to test the installed frame components before or after manufacture to determine the stress in those components. After installation, there is no low cost test; testing cannot be achieved through the application of strain gauges because strain gauges work only on incremental change arising as a result of strain. They can only be utilized if the strain gauge is attached before a strain occurs in the specimen of interest. One approach is x-ray testing. It is particularly limited. This novel procedure enables testing without having access to the unstressed frame member before stress is placed on the frame member. Alternatively, the frame member can be tested solely for residual stress before installation. Moreover, the procedure disclosed herein can be quickly implemented and the equipment easily affixed on and removed from the specimen undergoing test. Again, assume that a framework for supporting heavy equipment is to be tested. In this context, the frame members may terminate in a lattice work at suitable fasteners, and access to the frame members is easily achieved. This apparatus enables the testing of stress (both residual and loading stress) in the frame members at intermediate points without access to the ends of the frame members.

Other advantages depend on a variety of circumstances in application of this procedure. It is therefore summarized as a procedure for determining stress in a ferromagnetic member utilizing an applied magnetic field to the member and measuring the change of velocity in ultrasonic waves transmitted through the test specimen.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 3:
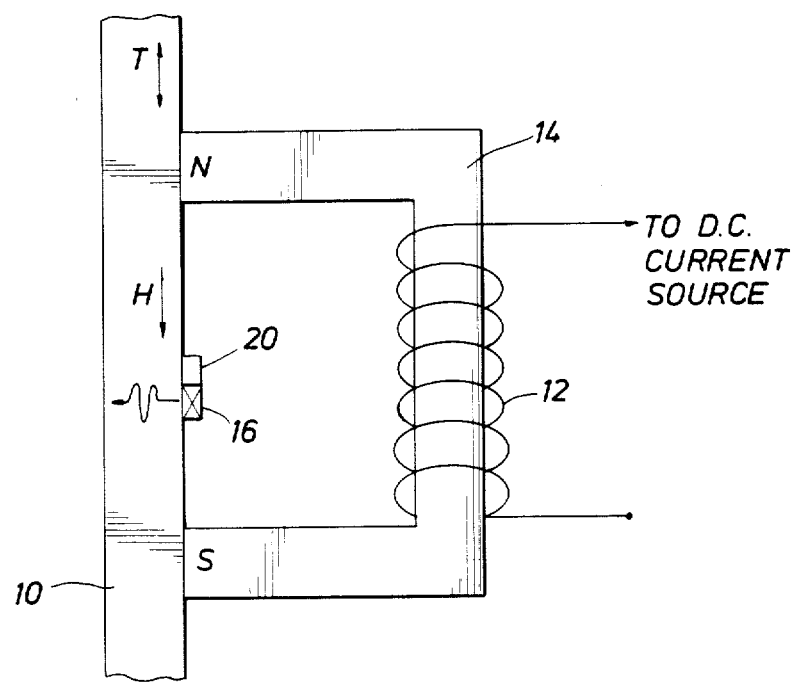
FIG. 3 shows a test apparatus installed for testing a specimen to determine the relationship between stress, magnetic field and shear or longitudinal wave propagation direction.
Figure 4:
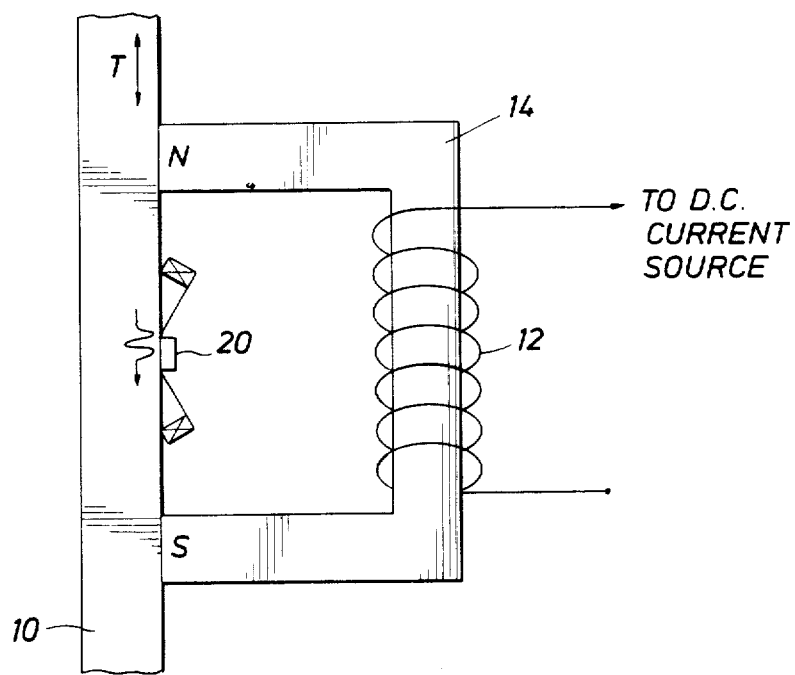
FIG. 4 is a test apparatus for testing with an ultrasonic surface wave.

Attention is first directed to FIGS. 3 and 4 of the drawings. There, a specimen 10 is undergoing testing. The specimen is presumed to be of plate stock fabricated in a mill, or otherwise cut to shape. The specimen 10 is typically relatively thin across its width and has other dimensions which can be varied over a wide range. In calibration tests, suitable data was obtained from specimens approximately 60 centimeters long, 10 centimeters in width and about 0.6 centimeters thick to verify that the procedure described below is quite applicable to plate and sheet stock. This is not to eliminate testing with thicker materials; rather, the most common test circumstances are involved in sheet stock, plate and the like.

The specimen 10 is a ferromagnetic material such as polycrystalline steel of any suitable alloy which responds to the application of a magnetic field. To this end, a coil 12 on a U-shaped magnet 14 applies a magnetic field. They form magnetic flux in the specimen 10. The specimen 10 has dimensions sufficient to extend past the pole faces of the magnet 14. Flux is coupled into the specimen 10 and forms a more or less uniform magnetic field within the specimen. To make the magnetic field in the region between the pole pieces reasonably uniform, it is recommended that the width of the pole pieces be about two or three times larger than the gap between the two pole pieces.

A transducer or transducers 16 of appropriate wave mode and frequency are coupled to the specimen using a suitable couplant. The transducer 16 is used to generate and detect an ultrasonic wave of desired wave mode and frequency. The transducer 16 is electrically connected through coaxial cables to suitable ultrasonic equipment including an rf pulse generator and an rf receiver. The direction of wave propagation is either perpendicular (FIG. 3) or parallel (FIG. 4) to the surface of the specimen. For the case of FIG. 3, the propagated ultrasonic wave is reflected by the opposite face of the specimen and returned to the transducer. The returned ultrasonic wave is in turn detected by the transducer. The wave is repeatedly reflected back and forth between opposite faces of the specimen. Repetitive internal reflections of the wave are repeated until energy of the propagated ultrasonic wave is dissipated in the specimen via attenuation processes in the material. The echo signal(s) detected by the transducer are amplified by an rf receiver and then processed to measure the velocity change as a function of the magnetic field. For the case of FIG. 4, the propagated surface ultrasonic wave is sent by one transducer and it is detected by a separate transducer. This detected signal is amplified and processed to measure the change in velocity as a function of the magnetic field.

A tangential Hall effect probe 20 is positioned against the surface of the specimen 10 using a suitable clamp. It is located approximately at the midpoint of the magnet 14. It is installed there to measure the effective magnetic field strength in the specimen 10. The measurement is achieved at or near the surface.

Several practical observations regarding FIGS. 3 and 4 should be noted. The transducer 16 is coupled to the specimen using an appropriate couplant. To obtain reproducible results, it is essential to maintain the state of transducer coupling constant during the period time during which MIVC is measured. The transducer coupling can be held fixed by mechanically clamping the transducer with a suitable clamping device.

Figure 1B:
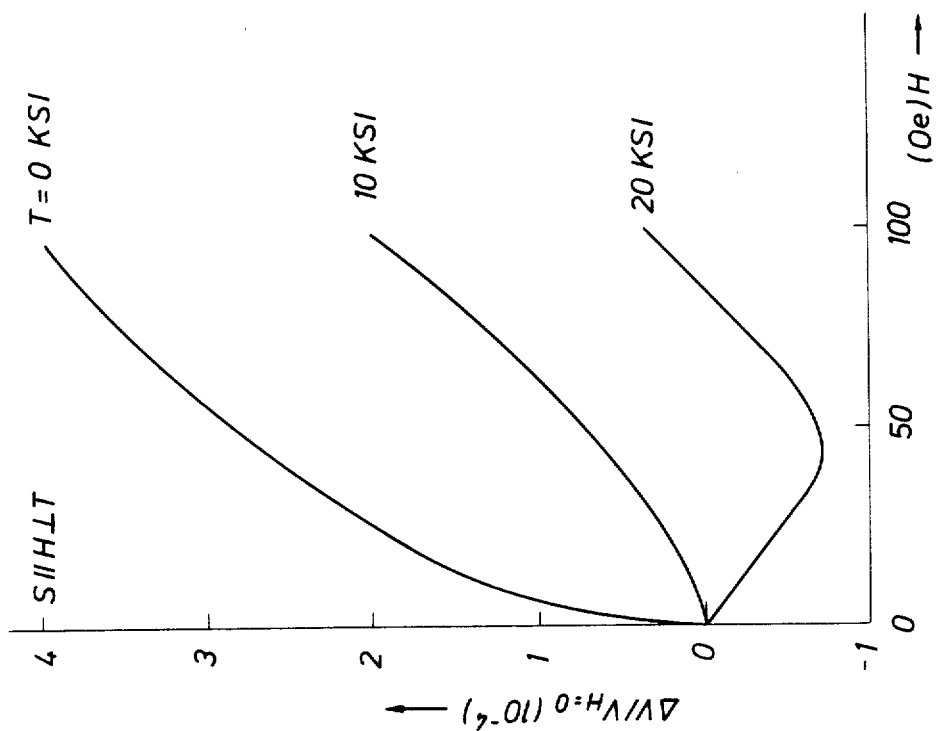
FIGS. 1A and 1B are graphs of field strength versus normallized velocity for various stress levels in a selected alloy.
Figure 1A:
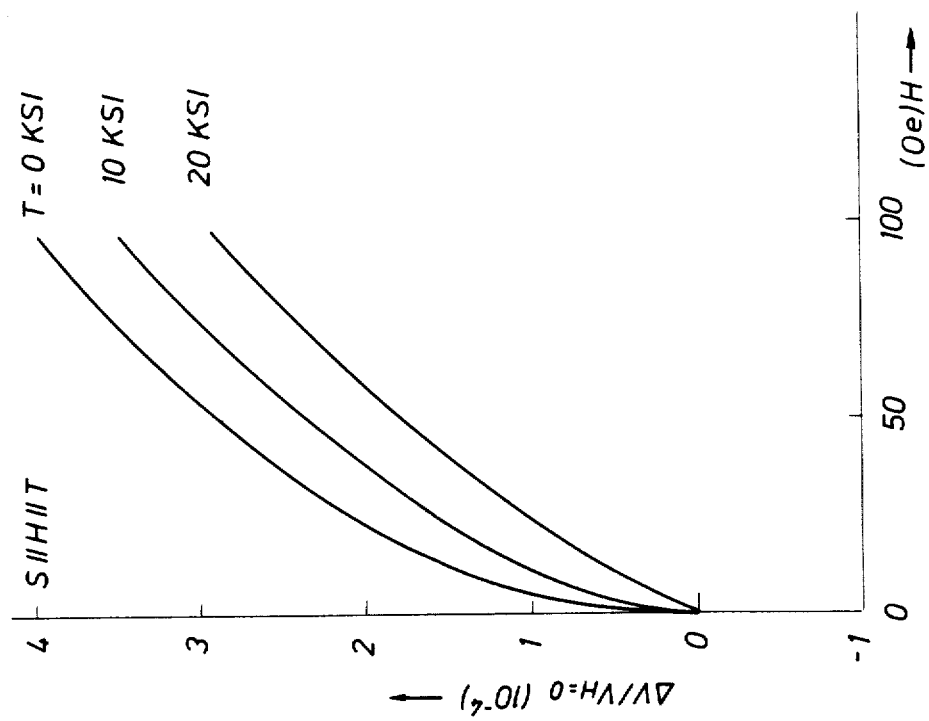
Figure 2A:
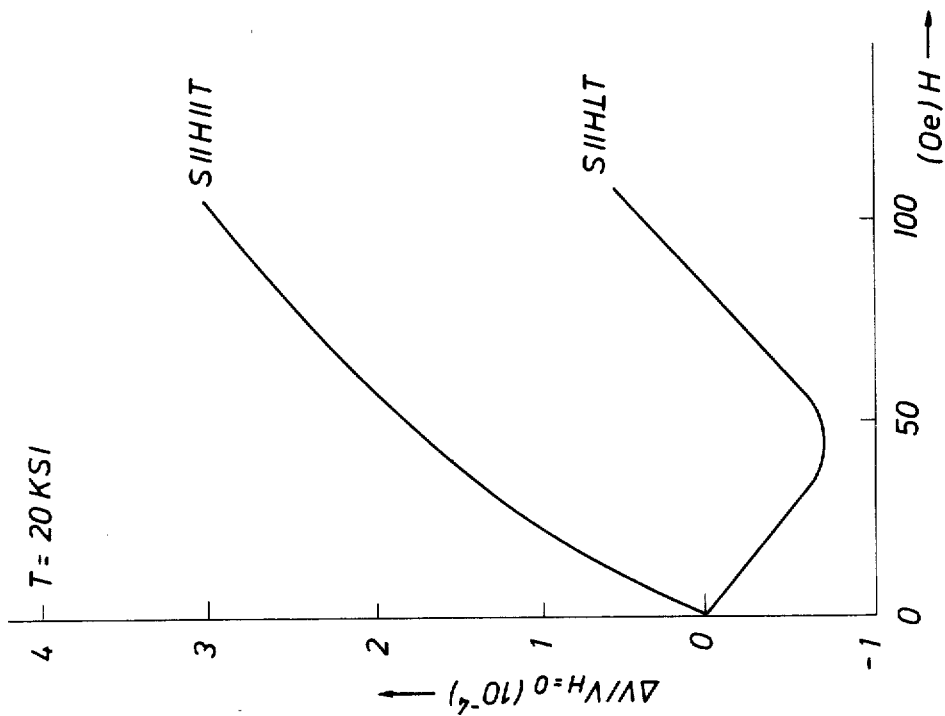
FIGS. 2A and 2B are different graphs showing angular repositioning of stress to the other variables.
Figure 2B:
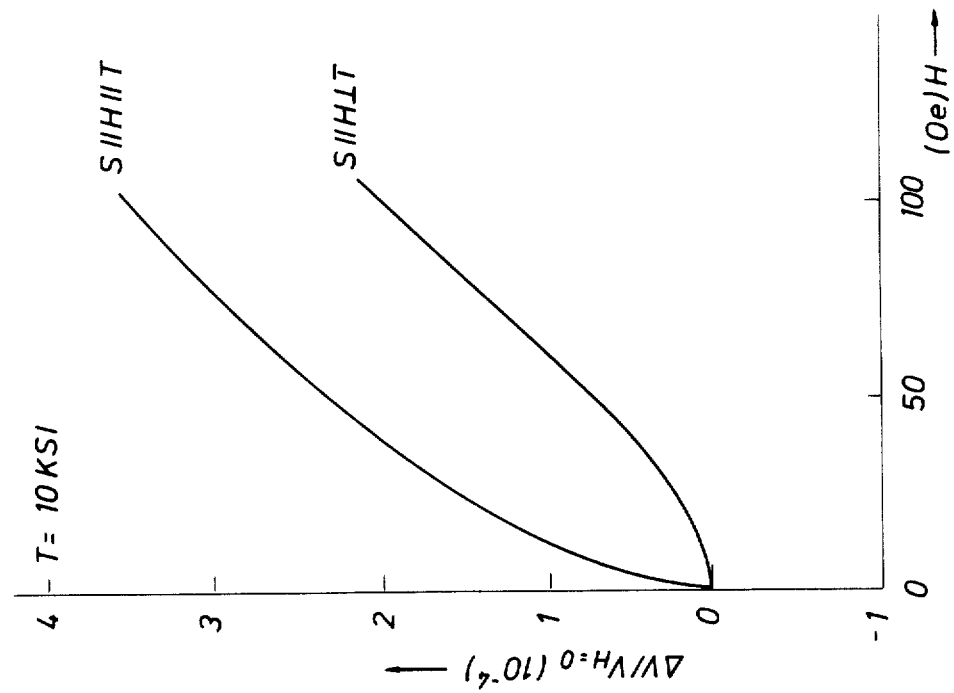

In FIG. 3, the transducer 16 is used to propagate a wave having a direction of propagation perpendicular to the surface of the plate. The direction of propagation is from the transducer 16 through the plate where the ultrasonic wave is reflected by the opposite face and returned to the transducer. One transducer can be used both as transmitter and receiver. Through techniques that are known including the echo-overlapping method and the relative phase measuring technique, velocity changes can be measured. The velocity change is normally represented incrementally, that is, the increment of change over the velocity at zero magnetic field. The curves set forth in FIGS. 1 and 2 represent such a ratio. The transducer 16 is thus connected to test apparatus which indicates the incremental change in velocity divided by the velocity at zero magnetic field.

For testing a thick material, it is expected that the magnetic field in the material set up by a C-shaped magnet would not be uniform throughout the material thickness. Instead, the magnetic field strength is expected to decrease with the depth from the material surface on which the magnet is placed. To interpret measured MIVC data for determining the stress in this case, appropriate corrections need to be made to take into account the magnetic field strength variations with the depth. As the first order correction, the average magnetic field strength through the material thickness can be used. To this end, the magnetic field strength measured at or near the surface using the Hall effect probe 20 and the expected magnetic field gradient in the material, which may be determined either experimentally or analytically, can be used.

Experimentally, it has been determined that there is no significant magnetic hysteresis effect. Accordingly, the magnetic field can either increase or decrease to some quiescent value. Moreover, it makes no difference to the procedure described in this disclosure if the magnetic field were in the opposite direction of that shown in FIGS. 3 and 4. That is, the DC source could be reversed and the lines of flux would run in the opposite direction. That would pose no particular problem and would not change the nature of the test.

The procedures described above can be used for obtaining calibration curves. In this case, the specimen 10 is fabricated in such a way that an external load can be applied to the specimen. The symbol T in FIGS. 3 and 4 represents the direction of externally applied stress. To obtain calibration curves for surface waves, bending moments may be applied to the specimen. When a bending moment is applied to the specimen, one surface of the specimen is subjected to tensile stress while the opposite surface is subjected to compressive stress. However, for calibration it is preferred to use a specimen to an uniform stress rather than to use a specimen subjected to a bending moment.

Calibration curves have been accumulated and FIGS. 1 and 2 show an example of such curves. The conditions for the data in FIGS. 1 and 2 were obtained with 4.5 MHz ultrasonic shear waves using the specimen and test apparatus shown in FIG. 3. The direction of propagation of the shear wave, the applied magnetic field and the stress were positioned as described in FIGS. 1 and 2.

As will be understood, the particular set of curves for FIGS. 1 and 2 were obtained for A-36 steel; obviously, similar sets of curves can be obtained for other alloys.

The foregoing is directed to the preferred embodiment, the scope is determined by the claims which follow.

What is claimed is:

1. A method of determining the stress in a ferromagnetic material specimen comprising the steps of:
    (a) propagating an ultrasonic wave of suitable frequency and mode in a given direction through the specimen and detecting such a propagated wave;
    (b) applying a magnetic field to the specimen of a specified strength; and
    (c) measuring the change in velocity of the propagated ultrasonic wave in the specimen having the applied magnetic field to obtain an indication of stress in the specimen.

2. The method of claim 1 including the step of positioning a magnet having spaced pole faces against the specimen, and further forming a fixed field in the specimen between the pole faces.

3. The method of claim 1 including the step of forming the magnetic field in the specimen by flowing the DC current through a coil to form a magnetic field in a C-shaped magnet having a pair of spaced pole faces adapted to be facially contacted against the specimen.

4. The method of claim 3 including the step of measuring the magnetic field strength in the specimen between the pole faces.

5. The method of claim 4 including the step of measuring the magnetic field strength in the specimen by positioning a magnetic field strength measuring means against a surface of the specimen between the pole faces.

6. The method of claim 4 including the step of setting the magnetic field strength in the specimen to a specified level.

7. The method of claim 1 including the step of propagating an ultrasonic, longitudinal or shear wave in the specimen propagating from one surface of the specimen toward an opposing surface of the specimen for reflection thereby back toward the origin of the acoustic wavefront.

8. The method of claim 7 including the step of propagating an ultrasonic surface wave along the surface of the specimen.

9. The method of claim 7 including the step of propagating the ultrasonic wave at a location between a pair of magnetic pole faces on a C-shaped magnet positioned against the specimen so that the ultrasonic wave passes through a portion of the specimen exposed magnetic flux.

10. The method of claim 1 in repetitively testing a set of similar specimens including the step of releasably positioning a magnet to a specimen, the magnet having a pair of spaced pole faces to create a magnetic field in the specimen, and also attaching an ultrasonic transducer means to a surface of the specimen between the pole faces to obtain measurements of acoustic velocity change.

11. The method of claim 10 further including the step of positioning a magnetic field strength measuring means adjacent to the specimen to measure the magnetic field strength in the specimen.

12. The method of claim 11 wherein the magnetic field strength is measured between the pole faces.

13. The method of claim 1 including the step of propagating the ultrasonic wave repetitively at different frequencies, and measuring the change in velocity as a function of magnetic field strength.

14. The method of claim 13 including the step of transmitting the ultrasonic wave along the surface of the specimen.

15. The method of claim 1 including the step of comparing the measured MIVC to a set of calibration curves to determine the magnitude and the sign of the stress.

16. The method of claim 1 including the step of determining the direction of stress utilizing the characteristic dependence of MIVC on the relative orientation of stress, magnetic field, and propagation and/or polarization direction of the ultrasonic wave.

* * * * *